United States Patent [19]

Bröcker et al.

[11] Patent Number: 5,965,751
[45] Date of Patent: Oct. 12, 1999

[54] PROCESS FOR HYDROGENATION OF DIHYDROFURANS TO GIVE TETRAHYDROFURANS

[75] Inventors: Franz Josef Bröcker, Ludwigshafen; Rolf Fischer, Heidelberg; Gerd Kaibel, Lampertheim; Rolf Pinkos, Bad Dürkheim, all of Germany

[73] Assignee: BASF Aktiengesellschaft, Ludwigshafen, Germany

[21] Appl. No.: 09/068,978

[22] PCT Filed: Nov. 18, 1996

[86] PCT No.: PCT/EP96/05071

§ 371 Date: May 22, 1998

§ 102(e) Date: May 22, 1998

[87] PCT Pub. No.: WO97/19939

PCT Pub. Date: Jun. 5, 1997

[30] Foreign Application Priority Data

Nov. 29, 1995 [DE] Germany ............... 195 44 405

[51] Int. Cl.$^6$ ............... C07D 307/08; B01J 23/44
[52] U.S. Cl. ............... 549/429; 502/326
[58] Field of Search ............... 549/429, 507; 502/326, 527

[56] References Cited

U.S. PATENT DOCUMENTS 4,254,039  3/1981  Murib et al. ............... 260/346.11
4,962,210  10/1990  Falling et al. ............... 549/429

FOREIGN PATENT DOCUMENTS 0 198 435    10/1986  European Pat. Off. .
B 0 524 216   9/1994  European Pat. Off. .
2-002880      3/1990  Japan .

*Primary Examiner*—John Kight
*Assistant Examiner*—Charanjit S. Aulakh
*Attorney, Agent, or Firm*—Oblon, Spivak, McClelland, Maier & Neustadt, P.C.

[57] ABSTRACT

In a process for the catalytic hydrogenation of 2,5- and 2,3-dihydrofuran with hydrogen to give tetrahydrofuran, use is made of a catalyst in which a metal or a plurality of metals have been deposited by vapor deposition or sputtering on a metal wire mesh or a metal foil as support.

12 Claims, No Drawings

PROCESS FOR HYDROGENATION OF DIHYDROFURANS TO GIVE TETRAHYDROFURANS

The present invention relates to an improved process for the catalytic hydrogenation of 2,5- and 2,3-dihydrofuran (DHF) with hydrogen to give tetrahydrofuran (THF).

According to EP-A 524 216, 2,5-dihydrofuran containing 3,4-epoxy-1-butene and crotonaldehyde as secondary components can be hydrogenated with hydrogen over nickel and platinum catalysts to give THF. According to the Examples 1 and 2, 3.6 and 3.7 g respectively of THF/h are formed per gram of nickel.

U.S. Pat. No. 4 254 039 describes the hydrogenation of 2,5-DHF to give THF over a palladium-carbon catalyst (5% of Pd on C). At a conversion of only 51%, about 2 g of THF/h are formed per gram of palladium.

The abovementioned processes have the disadvantage that either unsupported catalysts of the active metals or supported catalysts are used. These have a high proportion of active metals which can be only partially utilized for the actual catalytic step. However, if the expensive active content is reduced, the space-time yield becomes very low and the process thus becomes uneconomical.

It is an object of the present invention to find a process which gives high space-time yields for the hydrogenation of DHF to give THF while using small amounts of active composition.

We have found that this object is achieved by an improved process for the catalytic hydrogenation of dihydrofurans to give THF, wherein use is made of a catalyst in which a metal or a plurality of metals have been deposited by vapor deposition or sputtering on a metal wire mesh or a metal foil as support.

The catalysts of the present invention are produced by vapor deposition or sputtering of the active compositions onto a foil-like or mesh-like metal support. Metallic foils or meshes of materials having the material numbers 1.4767, 1.4401 and 1.4301 have been found to be particularly useful. These metallic support materials are generally pretreated by oxidative heat treatment, preferably in air, at from 600 to 1100° C., preferably from 750 to 1000° C., and subsequently coated with the active composition. After the coating step, a thermal activation in air can be carried out. For this activation, the coated support material can be heated in air at from 200 to 800° C., preferably from 300 to 700° C., for from 0.5 to 2 hours. The catalyst material thus produced can subsequently be shaped to form monoliths. After reduction of the catalyst with hydrogen at from 20 to 300° C., preferably from 20 to 200° C., which is advantageously carried out in the reactor, the catalyst is ready for use. In the case of noble metal catalysts, the reaction can also be started directly, without prior activation.

The methods of vapor deposition and sputtering of metals under reduced pressure are described in detail in "Handbook of Thin Film Technology", Maissel and Glang, McGraw Hill, N.Y., 1970, "Thin Film Processes", J. L. Vossen and W. Kern, Academic Press N.Y. and also in EP-A 198 435.

Suitable active compositions are in principle metals and metal combinations of the metallic elements of the Periodic Table, preferably metals of transition groups I, VII and VIII of the Periodic Table of the Elements, e.g. nickel, copper, cobalt, ruthenium, rhodium, palladium, rhenium, iridium and platinum; particular preference is given to palladium.

The hydrogenation can be carried out at from 10 to 250° C., preferably from 20 to 200° C., particularly preferably from 30 to 150° C., and at a hydrogen pressure of from 0.5 to 300 bar, preferably from 0.7 to 200 bar, particularly preferably from 1 to 100 bar.

The hydrogenation is advantageously carried out in a pressure apparatus, for example in a tube reactor, in the liquid phase, either in downflow or upflow operation, or in the gas phase.

The reactor feed preferably consists of pure 2,5- or 2,3-DHF or mixtures of the two, but it can also contain secondary components (up to 5% by weight) such as crotonaldehyde, butyraldehyde, vinyloxirane and water and/or inert diluents (up to 90% by weight) such as THF, dioxane or alcohols such as n-butanol.

The hydrogenation according to the present invention of DHF proceeds highly selectively. A by-product which forms in small amounts, primarily at very low hydrogen pressures, is furan. However, this can easily be separated from THF by distillation, so that 99.99% pure THF can be obtained in a simple way.

Dihydrofurans can be prepared by the methods described in U.S. Pat. No. 5,034,545, U.S. Pat. No. 5,082,956 or BE-A 674 652.

THF is used as a large-scale, industrial product, e.g. as solvent or starting material for poly-THF.

The process of the present invention makes possible weight ratios of active composition to THF formed per hour of up to 15,000.

EXAMPLES

All figures for the compositions of starting solutions or product solutions are in % by weight.

Example 1

Plain-woven wire mesh of the material no. 1.4767 having a mesh opening of 0.18 mm and a wire diameter of 0.112 mm was heated in air at 900° C. for 5 hours. Subsequently, the support mesh thus pretreated had 6 nm of palladium vapor-deposited on both sides in an electron beam vapor deposition unit. The thickness of the layer was measured by means of a crystal oscillator and the vapor deposition rate was controlled using the crystal oscillator. The amount of vapor-deposited palladium was 138 mg/m$^2$. This catalyst mesh was formed into monolithic bodies. For this purpose, part of the mesh was corrugated by means of a toothed roller. This corrugated mesh was laid together with smooth mesh and rolled up. This gave monolithic bodies which were fastened by point welding.

Example 2

Two catalyst monoliths each having a height of 20 cm and a diameter of 2 cm were made from 0.112 m$^2$ [sic] catalyst mesh as described in Example 1 and installed in a tube reactor at a mesh density of 1.79 m$^2$/l corresponding to 0.247 g of Pd/l. The catalyst was first reduced with H$_2$ for 2 hours at 150° C. After the reactor system had cooled, 2,5-dihydrofuran was pumped at 50° C. and atmospheric pressure together with hydrogen over the catalyst in the upflow mode with recirculation. The throughput per unit cross-sectional area was 250 m$^3$/m$^2$ h for 2,5-dihydrofuran and 220 m$^3$/m$^2$ h for H$_2$. The space-time yield was 0.34 kg of THF/l of cat. h or 1375 g of THF/g of Pd h. Gas-chromatographic analyses of starting material and hydrogenation product gave the following values:

Starting material: 2,5-DHF: 99.0%, 2,3-DHF: 0.1%, THF: 0.85%, furan: 0.05%

Produkt: THF: 98.6%, furan: 1,4%

Example 3

Using a method similar to Example 2, 2,5-dihydrofuran was hydrogenated in a pressure apparatus at 80° C. and 20 bar in the upflow mode with recirculation. The throughput per unit cross-sectional area was 90 m$^3$/m$^2$ h for 2,5-dihydrofuran and 10 m$^3$/m$^2$ h for H$_2$. The space-time yield was 1.65 kg of THF/l of cat. h. Based on the amount of catalyst mesh installed of 2.338 m$^2$/l corresponding to 0.322 g of Pd/l, the yield based on the active composition was 5120 g of THF/g of Pd h. Gas-chromatographic analyses of the starting material and hydrogenation product gave the following values:

Starting material: 2,5-DHF: 98.99%, 2,3-DHF: 0.07%, THF: 1.01%, furan: 0.04%

Product: THF: 99.7%, furan: 0.3%

We claim:

1. A process of hydrogenation, comprising:
   hydrogenating 2,5- and 2,3-dihydrofuran with hydrogen in the presence of a catalyst prepared by vapor depositing or sputtering at least one metal selected from the group consisting of the transition metals of Groups I, VII and VIII of the Periodic Table on a support of a metal wire mesh or metal foil.

2. The process as claimed in claim 1, wherein said catalyst is activated in air at elevated temperature prior to use.

3. The process as claimed in claim 1, wherein the hydrogenation is conducted at a temperature ranging from 10–250° C.

4. The process as claimed in claim 3, wherein said temperature range is from 20–200° C.

5. The process as claimed in claim 4, wherein said temperature range is from 30–150° C.

6. The process as claimed in claim 1, wherein the hydrogenation reaction is conducted under a hydrogen pressure of 0.5–300 bar.

7. The process as claimed in claim 6, wherein said hydrogenation pressure range is from 0.7–200 bar.

8. The process as claimed in claim 7, wherein said hydrogen pressure range is from 1–100 bar.

9. The process as claimed in claim 1, wherein said transition metal is nickel, copper, cobalt, ruthenium, rhodium, palladium, rhenium, iridium or platinum.

10. The process as claimed in claim 1, wherein said hydrogenation reaction is conducted in a tube reactor in the liquid phase or in the gas phase.

11. The process as claimed in claim 2, wherein the metal wire mesh or metal foil support is heated in air at a temperature of 600–1100° C. prior to metal deposition thereon.

12. The process as claimed in claim 1, wherein said catalytically active metal is palladium.

* * * * *